(12) United States Patent (10) Patent No.: US 10,896,743 B2
Kim (45) Date of Patent: Jan. 19, 2021

(54) SECURE COMMUNICATION OF NUCLEIC ACID SEQUENCE INFORMATION THROUGH A NETWORK

(71) Applicant: CIPHEROME, INC., Cupertino (CA)

(72) Inventor: Ju Han Kim, Seoul (KR)

(73) Assignee: Cipherome, Inc., Cupertino, CA (US)

( * ) Notice: Subject to any disclaimer, the term of this patent is extended or adjusted under 35 U.S.C. 154(b) by 440 days.

(21) Appl. No.: 15/321,135

(22) PCT Filed: Jun. 24, 2015

(86) PCT No.: PCT/KR2015/006427
§ 371 (c)(1),
(2) Date: Dec. 21, 2016

(87) PCT Pub. No.: WO2015/199440
PCT Pub. Date: Dec. 30, 2015

(65) Prior Publication Data
US 2017/0140095 A1    May 18, 2017

(30) Foreign Application Priority Data

Jun. 24, 2014 (KR) .................. 10-2014-0077019
Jun. 23, 2015 (KR) .................. 10-2015-0088901

(51) Int. Cl.
*G16B 30/00* (2019.01)
*G06F 21/62* (2013.01)

(52) U.S. Cl.
CPC ......... *G16B 30/00* (2019.02); *G06F 21/6254* (2013.01)

(58) Field of Classification Search
None
See application file for complete search history.

(56) References Cited

U.S. PATENT DOCUMENTS

2005/0107961 A1   5/2005   Uemura et al.
2014/0372046 A1   12/2014  Chung et al.

FOREIGN PATENT DOCUMENTS

| JP | 2003-242154 A | 8/2003 |
|---|---|---|
| KR | 10-2013-0075559 A | 7/2013 |
| KR | 10-2013-0122816 A | 11/2013 |
| WO | WO 2013/116782 A1 | 8/2013 |
| WO | WO 2013/178801 A2 | 12/2013 |

OTHER PUBLICATIONS

Troncoso-Pastoriza, Juan Ramón, Stefan Katzenbeisser, and Mehmet Celik. "Privacy preserving error resilient DNA searching through oblivious automata." Proceedings of the 14th ACM conference on Computer and communications security. ACM, 2007.*
Korean Second Office Action, Korean Application No. 10-2015-0088901, dated May 23, 2016, 13 pages.
Korean Second Office Action, Korean Application No. 10-2015-0088901, dated Feb. 27, 2017, 7 pages (with concise explanation of relevance).
PCT Written Opinion, PCT Application No. PCT/KR2015/006427, dated Oct. 8, 2015, 11 pages.
PCT International Search Report, PCT/KR2015/006427, dated Oct. 8, 2015, 4 Pages.

* cited by examiner

*Primary Examiner* — G Steven Vanni
(74) *Attorney, Agent, or Firm* — Fenwick & West LLP

(57) ABSTRACT

A nucleic acid sequence security method comprises the steps of: (a) creating a plurality of composites each comprising at least one of target elements derived from a nucleic acid sequence of an analysis requester or disguising elements identical to or different from the target elements; and (b) providing the created plurality of composites to an analyst.

13 Claims, 6 Drawing Sheets

Specification includes a Sequence Listing.

| Genetic locus | Genetic locus | Genetic locus | Genetic locus | Genetic locus |
|---|---|---|---|---|
|  |  | T.E |  |  |
| T.E |  |  |  |  |
|  |  |  |  |  |
|  | T.E |  |  |  |
|  |  |  |  | T.E |

{ A , G , G }

| 10 | 12 | 15 | 300 | 332 |
|---|---|---|---|---|
| A | G |  | T | A |
|  | A | G |  | G |
| T | T | C | A | G |
|  |  |  | A | T |
| A | T |  | C | G |

[Fig. 6]

SEQUENCE LISTING

```
<160> NUMBER OF SEQ ID NOS: 7

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ggaatcaacc ggcggactga ttacaccc                                            28

<210> SEQ ID NO 2
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
```

```
gcgcacccgg cgaa                                                    14

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aataccgcag cgtga                                                   15

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aagcatcaac gggtg                                                   15

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gtagctacac cctgtc                                                  16

<210> SEQ ID NO 6
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gatcgcccag cga                                                     13

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gaaacgcggc                                                         10
```

SECURE COMMUNICATION OF NUCLEIC ACID SEQUENCE INFORMATION THROUGH A NETWORK

CROSS-REFERENCE TO RELATED APPLICATIONS

This application is the National Stage of International Application No. PCT/KR2015/006427, filed Jun. 24, 2015, which claims the benefit of and priority to KR 10-2015-0088901, filed Jun. 23, 2015, and KR 10-2014-0077019, filed Jun. 24, 2014, each of which is herein incorporated in its entirety by reference.

SEQUENCE LISTING

The instant application contains a Sequence Listing which has been submitted electronically in ASCII format and is hereby incorporated by reference in its entirety. Said ASCII copy, created on Apr. 30, 2019, is named 34330US_CRF_sequencelisting.txt and is 2,063 bytes in size.

TECHNICAL FIELD

The present invention relates to nucleic acid sequence security technology and, more specifically, to a nucleic acid sequence security method capable of analyzing a nucleic acid sequence of an analysis requester without exposing the nucleic acid sequence of the analysis requester to an analyst, to a nucleic acid sequence apparatus, and to a recording medium storing the same.

BACKGROUND ART

A genome refers to the overall nucleotide sequences of chromosomes of an individual. The genome is the sum total of almost complete genetic information of one a biological species, and stores nucleic acid sequence information. Human genome has about 3.2 billion pairs of nucleotides, including all genes and regions other than the genes necessary to make one human individual, and is divided into 22 pairs of 44 autosomes and one pair of two sex chromosomes (X, Y) and mitochondria. Nucleic acids of the genome are double helical type of materials composed of adenine (A), thymine (T), guanine (G), and cytosine (C) bases, together with phosphates and sugars. Genetic information is encoded by an arrangement of the sequence of the four bases of the nucleic acid.

Human genes each have an arrangement of hundreds or thousands of amino acids, and provide a design drawing for every protein produced in the body. Human genes are estimated to be about 30,000-50,000 in number, and account for about 3-5% of the entire genome. About 30,000-50,000 human genes are encoded by nucleotide sequences, and of these, only a small part has revealed meanings. The genotypes of 95-97% of the nucleic acid sequences of the genome, which do not belong to the gene region, also have numerous sites involved in phenotypes of an individual, and the medical meanings thereof have also been continuously revealed. The interpretation of medical and biological meanings of the genetic information encoded by nucleotide sequences is being continuously developed. Therefore, an individual who first analyzes nucleotide sequences may need repetitive references and interpretations for his or her own nucleotide sequence information, in order to check whether newly found genome nucleotide sequence interpretation information applies to him or her.

The development of the nucleotide sequence analysis technique has reduced the costs required for analysis, and has allowed each individual to analyze the human genome and utilize genome information. Accordingly, many people retain their own genetic characteristics, that is, genetic nucleotide sequence information, and the risks of disease incidences and related phenotypes may be calculated through the genome nucleotide sequence information possessed by an individual. Therefore, the genome nucleotide sequence information of an individual is classified as sensitive information of which the exposure is burdensome, and thus, the exposure thereof to other peoples should be avoided, if possible. However, calculation methods necessary for the interpretation of the individual's own genotype information and information resources necessary therefor are possessed by an analyst or analyzing institution holding analysis equipment for information interpretation and analysis methods, and thus, an individual needs to transmit his or her own genotype information to the analyst or analyzing institution to calculate the probability of occurrence of his or her own phenotype from his or her own genotype information. This transmission of the genotype information has a disadvantage in that the risk of the exposure of the individual's genotype information is increased.

Korean Patent Application Publication No. 10-2013-0075559 pertains to a method for managing genetic information, and more specifically, discloses a method wherein the individual's genetic information is divided into a plurality of partial sequences, stored, and managed, so that when the stored information is hacked or leaked, the divisionally stored information is difficult to recover to the original state before the division. The above patent application pertains to the security at the time of storing and keeping sensitive genetic information, and thus is differentiated from the present invention relating to the information security management technology wherein an individual or organization, holding genetic information to be analyzed, transmits nucleic acid sequence information to an analyst or analyzing institution and is involved in the procedure of receiving the analyzed results. The published patent application has disadvantages in that, if the identifier information is exposed, the individual genetic information may be exposed, and the identifier's information itself is vulnerable to security.

DETAILED DESCRIPTION OF INVENTION

Technical Problem

An embodiment of the present invention is to provide a nucleic acid sequence security method, capable of analyzing a nucleic acid sequence of an analysis requester without exposing the nucleic acid sequence of the analysis requester to an analyst.

An embodiment of the present invention is to provide a nucleic acid sequence security method, capable of analyzing a nucleic acid sequence of an analyst requester through a sparse matrix which expresses composites each including a target element derived from a nucleic acid sequence of an analysis requester and a disguising element and is defined in view of a plurality of target elements.

An embodiment of the present invention is to provide a nucleic acid sequence security method capable of determining the number of a plurality of composites each including a target element and a disguising element or the size of each of the plurality of composites to set the security strength of a nucleic acid sequence.

An embodiment of the present invention is to provide a nucleic acid sequence security method capable of receiving interpretation results of a plurality of composites from an analyst to obtain interpretation results of a nucleic acid sequence without the exposure of the nucleic acid sequence of an analysis requester.

An embodiment of the present invention is to provide a nucleic acid sequence security method capable of keeping inherent information or knowhow, such as the odds ratio for individual nucleotides, possessed by an analyst, by transmitting unit-based interpretation results of a nucleic acid sequence, in view of the analyst.

An embodiment of the present invention is to provide a nucleic acid sequence security method capable of minimizing the calculation load of a nucleic acid sequence security apparatus and improving the level of security.

Technical Solution

Among embodiments, a nucleic acid sequence security method includes: creating a plurality of composites each comprising at least one of target elements derived from a nucleic acid sequence of an analysis requester or disguising elements identical to or different from the target elements; and providing the created plurality of composites to an analyst.

Here, step (a) may include a step of expressing the plurality of composites by a sparse matrix with respect to a plurality of target elements. In addition, step (a) may further include a step of, if a corresponding target element is included in a corresponding composite, determining the location of the corresponding target element.

In an embodiment, step (a) may further include a step of defining a target element cell of the sparse matrix by a nucleotide-locus set comprising at least one nucleotide and genetic locus of the target element. In another embodiment, step (a) may further include a step of defining a target element cell of the sparse matrix by at least one nucleotide set associated with a genetic locus. In addition, step (a) may further include a step of dynamically determining the location of a target element cell of the sparse matrix to create a target element map necessary for a decoding procedure.

In an embodiment, step (a) may further include a step of extracting at least one nucleotide and genetic locus from the nucleic acid sequences to create the target elements. In another embodiment, step (a) may further include a step of segmenting the nucleic acid sequence into partial nucleotide sequences to create the target elements.

Here, step (a) may include a step of creating at least one disguising element of the corresponding composite on the basis of the similarity with the target element. In addition, step (a) may further include a step of creating at least one disguising element, of which the genetic distance or evolutional distance from the target element is a predetermined distance or smaller. In addition, step (a) may include a step of determining the number of the composites or the size of each of the composites according to the security strength set by the analysis requester.

Here, step (b) may further include a step of dividing the created plurality of composites to provide the divided composites to a plurality of direct or indirect analysts.

The method may further include (c) receiving a plurality of analysis composites showing interpretation results of the plurality of composites from the analyst, to obtain analysis results of the nucleic acid sequence.

Here, step (c) may further include a step of determining a plurality of target analysis elements showing the interpretation results of the plurality of target composites on the basis of a target element map. In addition, step (c) may further include a step of combining the determined plurality of target analysis elements to calculate the posterior odds of the analysis requester.

Among embodiments, a nucleic acid sequence security apparatus includes: a composite creator for creating a plurality of composites each including at least one of target elements derived from a nucleic acid sequence of an analysis requester or disguising elements identical to or different from the target element; and a composite provider for providing the created plurality of composites to an analyst.

The apparatus may further include an analysis composite interpreter for receiving a plurality of analysis composites showing interpretation results of the plurality of composites from the analyst to obtain analysis results of the nucleic acid sequence.

Here, the analysis composite interpreter may determine a plurality of target analysis elements showing the interpretation results of the plurality of target elements on the basis of a target element map. In addition, the analysis composite interpreter may combine the plurality of the determined plurality of target analysis elements to calculate the posterior odds of the analysis requester.

Among exemplary embodiments, a recording medium storing a computer program about a nucleic acid sequence security method includes: a function of creating a plurality of composites each including at least one of target elements derived from a nucleic acid sequence of an analysis requester or disguising elements identical to or different from the target elements; and a function of providing the created plurality of composites to an analyst.

The recording medium may further include a function of receiving a plurality of analysis composites showing the interpretation results of the plurality of composites from the analyst to obtain analysis results of the nucleic acid sequence.

Effects of Invention

The present disclosure can have the following advantages. However, it doesn't mean that particular embodiments need to encompass all the following advantages or only the following advantages, and thus the scope of the disclosure is not construed to be limited thereto.

The nucleic acid sequence security method according to an embodiment of the present invention can analyze the nucleic acid sequence of the analysis requester without the exposure of the nucleic acid sequence of the analysis requester to an analyst.

The nucleic acid sequence security method according to an embodiment of the present invention can analyze the nucleic acid sequence of the analyst requester through a sparse matrix which expresses composites each including a target element derived from the nucleic acid sequence of the analysis requester and a disguising element and is defined in view of a plurality of target elements.

The nucleic acid sequence security method according to an embodiment of the present invention can determine the number of a plurality of composites each including a target element and a disguising element or the size of each of the plurality of composites to set the security strength of the nucleic acid sequence.

The nucleic acid sequence security method according to an embodiment of the present invention can receive interpretation results of a plurality of composites from an analyst to obtain interpretation results of the nucleic acid sequence without the exposure of the nucleic acid sequence of the analysis requester.

The nucleic acid sequence security method according to an embodiment of the present invention can keep inherent information or knowhow, such as the odds ratio for individual nucleotides, possessed by the analyst, by receiving unit-based interpretation results of the nucleic acid sequence in view of the analyst.

The nucleic acid sequence security method according to an embodiment of the present invention can minimize the calculation load of the nucleic acid sequence security apparatus and improve the level of security.

BRIEF DESCRIPTION OF DRAWINGS

FIG. 3 discloses SEQ ID NOS 1-7, respectively, in order of appearance.

FIG. 4 discloses SEQ ID NO: 1.

MODE FOR IMPLEMENTING INVENTION

The description of the present invention merely corresponds to embodiments for illustrating structural and functional description, and thus the scope of the present invention is not construed to be limited to the embodiments described herein. In other words, the embodiments may become various modifications or may have several forms, and thus the scope of the present invention is construed to encompass equivalents capable of implementing the technical scope of the present invention. In addition, it doesn't mean that particular embodiments need to encompass all of the the objects or advantages presented by the present invention or only the advantages, and thus the scope of the disclosure is not construed to be limited thereto.

Meanwhile, the meaning of the terminology described herein shall be understood as follows.

The terminologies, such as "first" and "second", may be used to differentiate one element from another element, and the scope of the present invention is not limited by such terminologies. For example, a first element may be referred to as a second element and vice versa.

It shall be understood that, when one element is "connected" to another element, one element may be directly connected to another element, but a third element may be present therebetween. Whereas, it shall be understood that, when one element is "directly connected" to another element, no third element is presented therebetween. Meanwhile, the other expressions illustrating the relationship between elements, that is, "between" and "directly between", "adjacent to" and "directly adjacent to", or the like, are also shall be construed in the same manner.

It shall be understood that a singular expression may include a plural expression unless it clearly expresses different meaning in context, and it shall be noted that the terms, such as "include" and "have", are intended to indicate that a feature, a figure, a step, an operation, a constitutional element, a part, or a combination thereof may exist, but are not intended to exclude in advance the possibility of existence or addition of one or more other features, figures, steps, operations, constitutional elements, parts, or combinations thereof.

Reference numerals (for example, a, b, c, etc.) in the respective step are used for convenience of illustration, and do not illustrate the order of the respective steps. Unless the particular order is not clearly described in the context, the respective steps may occur in an order different from the specified order. That is, the respective steps may occur in an order the same as the specified order, may be substantially carried out at the same time or in the reverse order.

The present invention can be implemented on a computer-readable recording medium using the codes readable by a computer, and the recording medium includes all kinds of recording devices that store data to be read by a computer system. Examples of the computer-readable recording medium include a ROM, RAM, CD-ROM, magnetic tape, floppy disk, optical data storage device, and so on. Also, it may be implemented in the form of a carrier wave (e.g., transmission over Internet). In addition, the recording media readable by a computer are distributed in the computer systems connected through the network, so that the codes readable by the computers can be stored and implemented in a distribution manner.

The base is called a nucleobase or abbreviated to a base, and may include cytosine, guanine, adenine, thymine, and uracil, which are nitrogen bases found in deoxyribonucleic acid (DNA), ribonucleic acid (RNA), nucleotide, and nucleoside. The nucleotide is an organic molecule constituting a nucleic acid, such as DNA or RNA, and composed of a base-sugar-phosphate combination. The nucleic acid is a kind of polymeric organic material obtained by polymerizing nucleotides in a long chain shape.

The nucleic acid sequence may be implemented through an array, and the address of the array (i.e., index) is composed of genomic coordinate values (hereinafter, genetic loci, e.g., rsID number) and the data value stored in the array is composed of bases (e.g, A, G, T, C). Here, the bases may include genotypes. The genetic loci may have continuous values, or may have a list of discontinuous coordinate values extracted by selecting only necessary portions from different regions of the genome. When the genetic loci of the nucleic acid sequence have continuous coordinate values, the statement of only one among the addresses in the array clearly shows the other addresses in the array, and thus only one of the addresses in the array may be specified while the others are omitted.

The nucleic acid sequence of the individual genome may include the overall nucleic acid sequences of the genome of one individual, and may correspond to the nucleic acid sequence of an analysis requester.

A target nucleic acid sequence corresponds to a plurality of target elements associated with the nucleic acid sequence of the analysis requester, and may be created by extracting genetic locus-base pairs of the region to be analyzed from the individual genomic nucleic acid sequence and arranging the pairs in a predetermined order or by segmenting the individual nucleic acid sequence. In other words, the target nucleic acid sequence may be created by connecting a plurality of target elements in a predetermined order. The target nucleic acid sequence may be the entire region of the original individual genome nucleic acid sequence, a partial nucleotide sequence extracted from the individual genome nucleic acid sequence, or a nucleotide sequence obtained by combining partial nucleotide sequences extracted from several regions of the individual genome nucleic acid sequence.

In an embodiment of the present invention, the target nucleic acid sequence may be individual genetic information. Particularly, it was considered that, after the nucleotide sequence of the human genome is analyzed, an analysis of variations of a single nucleotide polymorphism (SNP) genomic nucleotide sequence on the basis of human race and individual varieties as well as an analysis of a simple interpretation of the genomic nucleotide sequence are actively being conducted currently. The polymorphism refers to an individual difference of the nucleotide sequence existing on the genome. The single nucleotide polymorphism represents an individual difference in a single base in the nucleotide sequence composed of A, T, C, and G, and there is the largest number of single nucleotide polymorphism in gene polymorphisms. All human beings are 99% identical in their genetic makeup, but a difference of single nucleotide polymorphism of about 0.1% induces individual and racial genetic characteristics, such as constitution, appearance, and disease, and therefore, for example, even the same drug used for persons results in different efficacies and responses. The individual difference of the nucleotide sequence includes various genetic variations, which are caused by base substitution, addition, or deletion, and may be expressed as single nucleotide variation (SNV) including a single nucleotide polymorphism, short tandem repeat polymorphism (STRP), or a polyalleic variation including various number of tandem repeat (VNTR) and copy number variation (CNV).

The target elements correspond to a partial nucleotide sequence derived from the nucleic acid sequence of an analysis requester. The target element may be created by extracting at least one nucleotide and genetic loci from the nucleic acid sequence of the analysis requester, or may be created by segmenting the nucleic acid sequence of the analysis requester into partial nucleotide sequences.

The disguising element may include a nucleotide sequence identical to or different from the target element in order that the target element is difficult to identify. The disguising element may be created by utilizing nucleic acid sequences existing in actual nature or referring nucleic acid sequences existing in actual nature. In an embodiment, the disguising element may be composed of a partial nucleotide sequence that is not identical to the target element, composed of a partial nucleotide sequence that is partially identical and partially non-identical to the target element, or composed of a partial nucleotide sequence that is identical to the target element. In another embodiment, the disguising element may be created by segmenting at least one nucleic acid sequence, created by referring to the nucleic acid sequence of the analyst requester or randomly created, into at least two partial nucleotide sequences, or may be composed of at least one nucleic acid sequence created by referring to the nucleotide sequence of target elements or randomly created.

The composite includes at least one of target elements or disguising elements identical to or different from the target elements. In other words, the composite may include the target element and the disguising element together, or may include only the disguising element or only the target element.

The analysis composite may exhibit interpretation results of the composite. For example, the analysis composite may include a set of interpretation results of the nucleic acid sequence corresponding to each of the element(s) contained in the composite. For another example, the analysis composite may include a set of nucleotide sequence-interpretation result pairs including nucleic acid sequences corresponding to element(s) included in the composite and the corresponding interpretation results together. The analysis composite may include interpretation results in the aspect in which the nucleic acid sequence information of the element(s) included in the composite is not displayed, or omitted, and is replaced with identifiers given for the differentiation of the corresponding nucleic acid sequence. The present invention can enable a high level of security through the changes in the size or number (the number of elements included in the composite) of the composite and the analysis composite.

Unless defined otherwise, all the terminologies used herein have the same meaning as those understood by a person having an ordinary skill in the art to which the present invention pertains. Terminologies as defined in a generally used dictionary should be interpreted to have the same meaning as those of the terminologies in context in the related descriptions, and shall not be interpreted in an ideal or excessively formal meaning unless they are explicitly defined herein.

Figure 1:
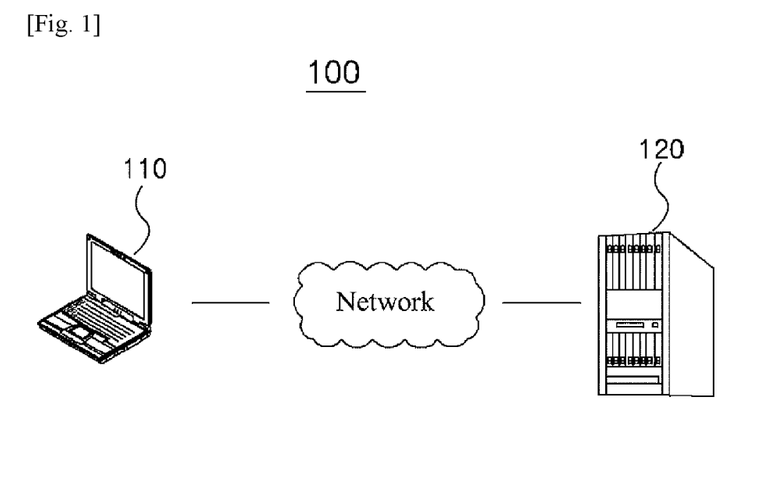
FIG. 1 is a diagram illustrating a nucleic acid sequence security system according to an embodiment of the present invention.

FIG. 1 is a diagram illustrating a nucleic acid sequence security system according to an embodiment of the present invention.

Referring to FIG. 1, a nucleic acid sequence security system 100 includes a nucleic acid sequence security apparatus 110 and an analysis server (hereinafter, analyst) 120, which may be connected through a network.

The nucleic acid sequence security apparatus 110 may request an analysis of the composite created on the basis of the nucleic acid sequence of an analysis requester, and may be implemented as, for example, a desktop, a notebook, a tablet PC, or a smartphone. The nucleic acid sequence of the analysis requester may be managed through a plurality of memory regions (a sparse matrix memory region and a target element map region which will be discussed later).

The analyst 120 may be connected with the nucleic acid sequence security apparatus 110 through a network, receive the composite from the nucleic acid sequence security apparatus 110, and analyze the received composite to provide an analysis composite to the nucleic acid sequence security apparatus 110.

Figure 2:
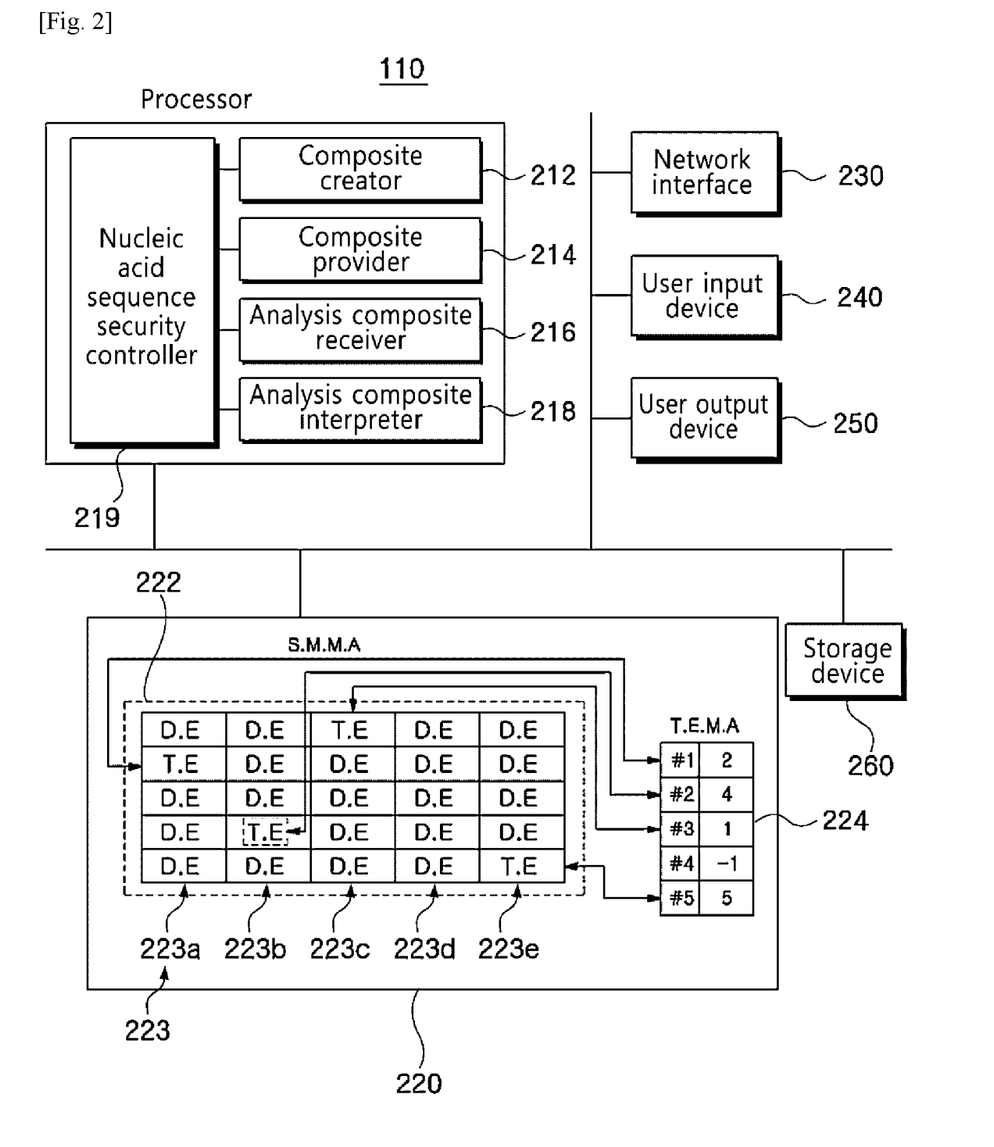
FIG. 2 is a block diagram illustrating a nucleic acid sequence security apparatus in FIG. 1.

FIG. 2 is a block diagram illustrating a nucleic acid sequence security apparatus in FIG. 1.

Referring to FIG. 2, the nucleic acid sequence security apparatus 110 includes a processor 210, a memory 220, a network interface 230, a user input device 240, a user output device 250, and a storage device 260.

The processor 210 includes a composite creator 212, a composite provider 214, an analysis composite receiver 216, an analysis composite interpreter 218, and a nucleic acid sequence security controller 219.

The composite creator 212 creates a plurality of composites each including at least one of target elements derived from the nucleic acid sequence of the analysis requester or disguising elements identical to or different from the target elements. The composite creator 212 may determine the location of the corresponding target element in the corresponding composite if the target element is included in the created composite. For example, the composite creator 212 may create a first composite including one target element, a second composite including four disguising elements, and a third composite including one target element and one disguising element, and determine the locations of the target elements included in the first composite and the third composite in the corresponding composites.

The composite creator 212 may express the plurality of composites by a sparse matrix with respect to a plurality of target elements. The composite creator 212 may dynamically determine the location of a target element cell in the sparse matrix to create a target unit map 224 necessary for a decoding procedure (of obtaining interpretation results of the target element from a plurality of analysis composites).

The composite creator 212 may determine the number of composites or the size of each of the composites according to the set security strength. The number of composites is associated with the number of columns of the matrix composed of the plurality of composites, and the size of each of the composites is associated with the number of rows of the matrix composed of the plurality of composites. The composite creator 212 may receive a security strength setting request from the analysis requester to create a plurality of composites satisfying the requested security strength.

The composite creator 212 may create a plurality of composites each including at least one of target elements or disguising elements to transmit the composites to the analyst, thereby providing a security method wherein the increase in the calculation load of the nucleic acid sequence of the analyst is remarkably lower than the increase in the security grade of the nucleic acid sequence.

Typical encoding technology is the procedure in which information K is transmitted in the form of E(K) by being converted into an encoding function (key) E while a receiver decodes the information as a decoding function (key) D, K=D(E(K)). Here, the encoding function and the decoding function corresponding to the security key are kept under individual responsibility, and the encoding technique is incapacitated when the security key is exposed. The security key is a kind of information, and thus the size thereof is a core of security. The simplest process for decryption is a random key creator (a technique of testing all combinations). Through this, all security keys are theoretically decryptable. For example, 4-digit security key may be decrypted by ten thousand attacks. Therefore, modern security algorithms use very large security keys, such as 32-bit security key, and thus the existing computer technology cannot test all cases within a proper time (e.g., 100 million years). Finally, the problem size is made larger to a realistically non-computable level.

Embodiments of the present invention target genetic information, which is the personal strong identification information, and thus is more similar to a problem of transmitting a security key itself rather than a problem of encoding and transmitting data. The present invention has an effect of enlarging a security key by distributing the security key into two or more elements capable of including a disguising key (all the extraction, segmentation, or extraction and combination of components constituting the security key are possible). For example, the composite creator 212 can enlarge the security key of the nucleic acid sequence by creating ten composites on the basis of the 100-length nucleic acid sequence, each of the composites including one target element (derived from the 100-length nucleic acid sequence) and four disguising elements.

For example, when the number of created composites is i and the number of elements included in each composite is j, the number of combinative extraction of the mixing thereof is $j^i$, and thus it is converted into a problem of finding one original key among $j^i$ combinable keys, so the size of the solving subject increases exponentially. For example, if i=10 and j=10, the size of the problem will increase to $10^{10}$, that is, 10 billion. In consideration of 16-bit security (65536), 32-bit security (4.3 billion), and 64-bit security ($1.8 \times 10^{19}$) as existing security technology for comparison, i=19 and j=10 is sufficient in order to obtain the similar level to the 64-bit security. That is, when the number of elements included in each composite is 2, the number of composites is equal to the number of security bits, and here the security level is $1/j^i$.

When the size of the solution subject is enlarged, it is important to solve the increase in the calculation load by a receiver, which is an analyst or analyzing institution. The computational complexity, which means the amount of interpretation or analysis operation carried out when the analyst or analyzing institution directly receives one original target nucleotide sequence, is varied depending on the corresponding algorithm, and may correspond to constant (K) irrelevant to the length of the inputted nucleic acid sequence of the analysis requester, a linear algorithm proportional to the corresponding length, a quadratic function proportional to the square of the corresponding length, or an exponential multiplication of the corresponding length.

That is, the present invention provides a very advantageous manner in which the increase (i*j) in the calculation load of the analyst 120 is remarkably low compared with the increase in the security grade of $j^i$ since the length of the nucleic acid sequence of the analysis requester is not varied but the calculation load of the analyst 120 is increased by the added multiple of the elements included in each composite. For example, the nucleic acid sequence security apparatus 110 creates ten composites by creating ten target elements on the basis of the nucleic acid sequence of the analysis requester and adding four disguising elements for each target element, thereby having a security grade increased by $5^{10}$ times. Here, the computational load of the analyst 120 increases by 5*10 times, which indicates a significantly low numerical value compared with the increase in the security grade.

The composite provider 214 provides the plurality of composites, created by the composite creator 212, to the analyst 120. The composite provider 214 may provide all of the plurality of created composites to the analyst, or may divide the plurality of created composites and provide the divided composites to a plurality of direct or indirect analysts. For example, the composite provider 214 may create six composites, and provide three composites to analyst A and three composites to analyst B.

The analysis composite receiver 216 receives a plurality of analysis composites showing interpretation results of the plurality of composites from the analyst 120. For example, the analysis composite receiver 216 may receive a first analysis composite showing interpretation results of the first composite, a second analysis composite showing interpretation results of the second composite, and a third analysis composite showing interpretation results of the third composite.

The analysis composite interpreter 218 acquires analysis results of the nucleic acid sequence through the plurality of received analysis composites. The analysis composite interpreter 218 may determine a plurality of target analysis elements corresponding to the interpretation results of the plurality of target elements from the plurality of analysis composites and deduce the final analysis results of the nucleic acid sequence of the analysis requester using the plurality of determined target analysis elements.

The nucleic acid sequence security controller 219 may control the overall operation of the nucleic acid sequence security apparatus 110, and may control the data flow among the composite creator 212, the composite provider 214, the analysis composite receiver 216, and the analysis composite interpreter 218.

The memory 220 includes a sparse matrix memory area (SMMA) and a target element map area (TEMA).

The sparse matrix memory area (SMMA) corresponds to a space that stores a sparse matrix 222 with respect to the plurality of composites 223 and the plurality of target elements included in the composites 223.

Each of the plurality of composites 223 may include at least one of target elements (TE) or disguising elements (DE). For example, composites 1, 2, 3, and 5 223a, 223b, 223c, and 223e include one target element and four disguising elements, and composite 4, 223d, includes five disguising elements.

In FIG. 2, the plurality of composites 223 include four target elements and 21 disguising elements, and the plurality of target elements and disguising elements included in the plurality of composites 223 may configure a matrix of 5 columns by 5 rows (the plurality of composites 223 each are located on the column of the configured matrix). Therefore, the plurality of composites 223 may be expressed by a sparse matrix 222 with respect to the plurality of target elements.

In FIG. 2, the sparse matrix 222 with respect to the plurality of target elements includes: as cells of the matrix, the target element of composite 1 223a at row 2, column 1; the target element of composite 2 223b at row 4, column 2; the target element of composite 3 223c at row 1, column 3; and the target element of composite 5 223e at row 5, column 5.

The target element map area (TEMA) corresponds to a space that stores the target element map 224 for the sparse matrix 222 stored in the sparse matrix memory area (SMMA).

The target element map 224 corresponds to a map for the locations of the plurality of target elements included in the sparse matrix 222. For example, the target element map 224 includes the locations of the target element on column 1 to the target element on column 5 if the number of columns of the sparse matrix 222 stored in the sparse matrix memory area (SMMA) is five. When the corresponding column of the sparse matrix 222 does not include a target element, the target element map 224 can differentiate the presence or absence of a target element by storing the location of the target element on the corresponding column as a minus value (e.g., −1).

The network interface 230 includes an environment for connection with the analyst 120 through the network, and may include an adaptor for, for example, local area network (LAN) communication.

The user input device 240 includes an environment for receiving a user input, and may include an adaptor, such as a mouse, a trackball, a touch pad, a graphic tablet, a scanner, a touch screen, a keyboard, or a pointing apparatus.

The user output device 250 includes an environment for outputting particular information (e.g., analysis results of the nucleic acid sequence of the analyst requester) to a user, and may include an adaptor, such as, a monitor or a touch screen.

In an embodiment, the user input device 240 and the user output device 250 may be connected through a remote connection.

The storage device 260 may be implemented as a non-volatile memory, such as a solid state disk (SSD) or a hard disk drive (HDD), and is used for storing data necessary for the nucleic acid sequence security apparatus 110.

Figure 3:
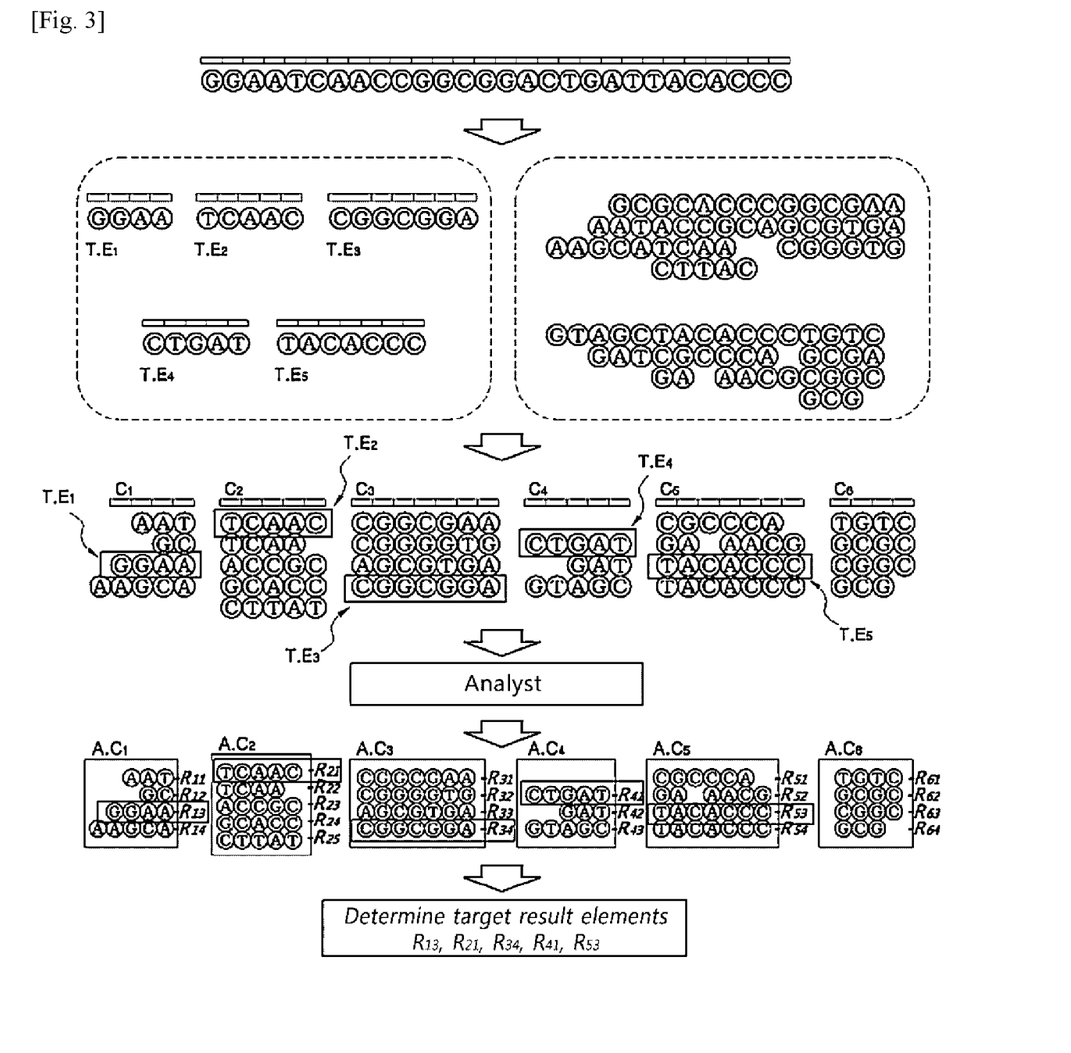
FIG. 3 is a diagram illustrating the creation of a plurality of composites and an interpretation procedure of a plurality of analysis composites according to an embodiment of the present invention.

FIG. 3 is a diagram illustrating the creation of a plurality of composites and an interpretation procedure of a plurality of analysis composites according to an embodiment of the present invention.

In FIG. 3, each nucleotide has a genetic locus (the genetic locus is a unique address/coordinate of the nucleotide, and may be expressed as a value, such as the location on a chromosome, a kind of coordinate value, the 1234501st location on chromosome 12, or rsID), and as such, many files are standardized and used as a file format containing genetic locus+nucleotide+other information. For example, variant call format (VCF) is a file format in which only an extracted individual variation region, rather than the entire sequence, is expressed as coordinates and detected genotype+other information. In an embodiment, the standardized format containing genetic locus+nucleotide+other information of the nucleic acid sequence of the analysis requester and the nucleic acid sequence included in the target element, disguising element, composite, or analysis composite may include variant call format (VCF), binary version of VCF (BCF), gene-finding format (GFF, generic feature format, current version 4.1), gene transfer format (GTF), genome variation format (GVF), sequence alignment map/binary version of SAM (SAM/BAM), QUAL, SCARF, QSEQ, IG, Maq, SOAP, bcf, pileup, mpileup, CASAVA, MaCH, GLFv2, GPFv2, axt, BED, BED15, BED detail, BEDPE, bedGraph, bigBed, bigWig, Chain, GenePred table, HAL, HDF5, MAF, Net, Personal Genome SNP, PSL, Wiggleformat (WIG), 2 bit, nib, CSFASTQ, CSFASTA, FASTA, FASTQ format or extension formats thereof. Here, for the target nucleic acid sequence, only the selected particular nucleotides (markers), such as single nucleotide polymorphism (SNP), may be selected and transmitted, or the entire successive sequence may be transmitted. The gene sequence is a sequence itself, in which nucleotides are listed in a predetermined order. Also, the present invention is directed to the security of the transmitted target nucleic acid sequence, and thus the transmitted sequence may be the original sequence or a partially selected sequence. In an embodiment, the nucleic acid sequence may be nucleotides determined from biallelic mutation, including single nucleotide polymorphism (SNP) at the particular gene or non-gene locus, and nucleotide substitution, addition, or deletion, or polyalleic mutation, including short tandem repeat polymorphism (STRP) or various number of tandem repeat (VNTR).

The composite creator 212 extracts at least one nucleotide and genetic locus from the nucleic acid sequence of the analysis requester to create a target element. In order to create the plurality of composites, the composite creator 212 may create target element T.E1 having a nucleic acid sequence of GAAT, target element T.E2 having a nucleic acid sequence of ACGCA, target element T.E3 having a nucleic acid sequence of TCCTGAT, target element T.E4 having a nucleic acid sequence of GACAC, target element T.E5 having a nucleic acid sequence of CCAGCA, in a manner of extracting at least one nucleotide and genetic locus from the nucleic acid sequence of the analysis requester.

Then, the composite creator 212 creates guising elements constituting the plurality of composites. In an embodiment, the composite creator 212 may create at least one disguising element in the corresponding composite, on the basis of similarity with the created target element. In another embodiment, the composite creator 212 may create at least one disguising element, of which the gene distance or evolutionary distance from the created target element is smaller than the particular distance.

Finally, the composite creator 212 may create composite C1 containing target element T.E1, composite C2 containing target element T.E2, composite C3 containing target element T.E3, composite C4 containing target element T.E4, target element, composite C5 containing target element T.E5, and composite C6 containing only a plurality of disguising elements without a target element. The composite creator 212, while creating the plurality of composites (C1-C6), may determine the locations of the target elements included in the composites. In FIG. 3, the composite creator 212 may dispose target element T.E1 at location No. 3 of composite C1, target element T.E2 at location No. 1 of composite C2, target element T.E3 at location No. 4 of composite C3, target element T.E4 at location No. 1 of composite C4, and last, target element T.E5 at location No. 3 of composite C5.

The plurality of created composites C1-C6 are provided to the analyst. The analyst 120 analyzes the received plurality of composites C1-C6 to provide a plurality of analysis composites 1 to 6 A.C1-A.C6 showing interpretation results of the plurality of composites C1-C6 to the analysis composite receiver 216. That is, the analyst 120 creates analysis result values that can be provided for the segmented nucleic acid sequences. For example, the composite creator 212 creates ten composites, and when each composite includes one target element and four disguising elements, the analyst 120 creates 50 analysis result values and transmits a plurality of analysis composites containing the created analysis result values to the nucleic acid sequence security apparatus 110. The nucleic acid sequence security apparatus 110 may receive the 50 analysis result values to extract ten interpretation or analysis result values (ten target analysis elements) of the target elements of the respective analysis composites while referring to the target element nucleotide sequence or the target element creation rule (e.g., target element location information, such as a target element map 224), and then combining the result values, thereby obtaining the same result values as the final products of the interpretation or analysis of the nucleic acid sequence of the analysis requester. Here, the function for combining ten result values of the target elements extracted from the analysis composites may be committed in advance, created/transmitted by the analysis institution, or requested by a client (e.g., the analysis requester). Here, the function includes various calculation methods, such as multiplying, adding, or averaging ten values.

In FIG. 3, the plurality of analysis composites A.C1-A.C6 include a plurality of target interpretation elements (R13, R21, R34, R41, and R53), respectively, corresponding to the plurality of target elements T.E1-T.E5 included in the plurality of composites C1-C6. The nucleic acid sequence security apparatus 110 holds nucleic acid sequence information of the target elements and disguising elements, which are requested to be analyzed, and thus can easily extract analysis results (here, R13, R21, R34, R41, and R53) logically connected with the sequences, which are identical to nucleic acid sequence information of corresponding target elements of the respective composites (in FIG. 3, T.E1 corresponds to GAAT; T.E2 corresponds to ACGCA; T.E3 corresponds to TCCTGAT; T.E4 corresponds to GACAC; and T.E5 corresponds to CCAGCG). Here, the analyst 120 does not need to transmit the nucleic acid sequence information by necessarily including the nucleic acid sequence information of the target elements and disguising elements in the respective elements included in the plurality of analysis composites, and thus can transmit the nucleic acid sequence information by reducing the amount of information through encoding or the like (logically, still differentiable reducing or encoding).

In an embodiment, the plurality of target interpretation elements R13, R21, R34, R41, and R53 may mean a set of nucleotide sequence-result value data pairs, connecting the nucleic acid sequence constituting the plurality of target elements and analysis result values of the corresponding nucleic acid sequence. In another embodiment, the plurality of target interpretation elements R13, R21, R34, R41, and R53 may mean a set of identifier-result value data pairs, in which the nucleic acid sequence information of the element(s) included in the composite is not displayed, or omitted and is replaced with identifiers given for the differentiation of the corresponding nucleic acid sequence.

The analysis composite interpreter 218 may determine a plurality of target interpretation elements R13, R21, R34, R41, and R53 corresponding to the plurality of target elements T.E1-T.E5 in the plurality of analysis composites A.C1-A.C6 received from the analyst on the basis of the target element map 224.

The analysis composite interpreter 218 may operate the determined plurality of target analysis elements R13, R21, R34, R41, and R53 using a particular function f(Rk), and deduce the final analysis results of the nucleic acid sequence of the analysis requester. For example, the analysis composite interpreter 218 may calculate the posterior odds of the analysis requester by combining the determined plurality of target analysis elements R13, R21, R34, R41, and R53, and the calculated posterior odds of the analysis requester may provide the final analysis results of the nucleic acid sequence of the analysis requester. Hereinafter, the calculation procedure of the the posterior odds of the analysis requester, which is carried out by the analysis composite interpreter 218, will be described in detail.

The analysis composite interpreter 218 may calculate the posterior odds of the nucleic acid sequence of the analysis requester (the disease risk of an individual having the corresponding nucleic acid nucleotide) according to the Bayes theorem. According to the Bayes theorem, the posterior odds may be expressed as the product of the prior odds and the likelihood ratio as shown in equation 1 below.

$$\text{Posteror Odds} = \text{Prior Odds} \times \text{Likelihood Ratio} \quad [\text{Equation 1}]$$

$$\frac{p(D \mid S)}{p(\overline{D} \mid S)} = \frac{p(D)}{p(\overline{D})} \cdot \frac{P(S \mid D)}{P(S \mid \overline{D})}$$

Here, the prior odds may be substituted with the neutral value, 1, without prior knowledge. Therefore, the posterior odds may be obtained through a chain calculation of continuously multiplying the prior odds value, 1 by the likelihood ratio. Here, the likelihood ratio according to the genotype may be calculated as shown in equation 2 below.

$$\text{Likelihood} = \frac{\text{(probability of the genotype in the case population)}}{\text{(probability of the genotype in the control population)}} \quad [\text{Equation 2}]$$

-continued $$LR = \frac{\text{probability of the genotype in the case population}}{\text{probability of the genotype in the control population}}$$

|  | AA | Aa | aa |
|---|---|---|---|
| Case | a | b | c |
| Control | d | e | f |
| LR | $\dfrac{\dfrac{a}{(a+b+c)}}{\dfrac{d}{(d+e+f)}}$ | $\dfrac{\dfrac{b}{(a+b+c)}}{\dfrac{e}{(d+e+f)}}$ | $\dfrac{\dfrac{c}{(a+b+c)}}{\dfrac{f}{(d+e+f)}}$ |

For example, when the likelihood ratios of respective locations of the nucleic acid sequence [a1, a2, . . . , an] composed of nucleotides G(a1), G(a2), . . . , G(an) obtained from n genetic loci a1, a2, . . . , an, are given, the posterior odds corresponding to the disease risk of an individual having the corresponding nucleic acid sequence may be calculated as shown in equation 3 below.

$$\text{Posterior Odds} = \prod_{i=1}^{n} G(a_i) \quad \text{[Equation 3]}$$

The analysis composite interpreter 218 may calculate the posterior odds of the nucleic acid sequence of the analysis requester using equation 3. For example, when the nucleic acid sequence security apparatus 110 determines k target elements from the nucleic acid sequence [a1, a2, . . . , an] of the analysis requester, the analysis composite interpreter 218 may calculate the final posterior odds of the nucleic acid sequence of the analyst requester by multiplying (performing a product operation) the posterior odds values (Rk) of k target elements, using the commutative property of multiplication (a×b=b×a) and the associative law of multiplication ((a×b)×c=a×(b×c)).

$$\text{Posterior Odds} = \prod_{k=1}^{k} (R_k) \quad \text{[Equation 4]}$$

In the present invention, Rk in equation 4 may correspond to the interpretation result value of the nucleotide, as a result of analysis of the target elements included in the plurality of analysis composites.

In equation 4, the variables are only k and Rk, and thus k and Rk may be determined in advance between the analysis requester and the analyst 120 or may be transmitted together with the plurality of analysis composites by the analyst 120. Alternatively, a corresponding equation necessary for the operation, together with analysis result values (R1-Rk) of at least one target element, may be requested by the analysis requester.

In addition, equation 4 is established regardless of the number of target elements or the length of the nucleic acid sequence of each target element. Therefore, the nucleic acid sequence security apparatus 110 can determine the number of target elements to be all numbers smaller than or equal to n. However, the segmentation of the locations in the nucleic acid sequence of the analysis requester one by one is not proper since the likelihoods LR(G(a1)), LR(G(a2)), . . . , LR(G(an)) of the respective locations, which are core knowledge properties in view of the analyst 120, are all exposed. The nucleic acid sequence security apparatus 110 needs to create target elements having a length of at least 2 for the protection of intellectual property such as an algorithm used to process data of the analyst 120. The length of the target elements may be varied according to the desired security strength setting. The security strength may increase exponentially with respect to the length of the target element, and thus a high security grade may be easily set. Whereas, when the target element is too long, and thus is close to the length of the nucleic acid sequence of the analyst requester, the possibility of the exposure of the target nucleic acid sequence of the receiver relatively increases, and therefore, in order to prevent this, the number of disguising elements included in the composite needs to be increased. Meanwhile, since the number of disguising elements and the security strength increase merely in a linear manner, the number needs to be significantly increased. However, this method is not unfavorable since it exponentially increases the analysis load of the analyst 120. Therefore, the present invention can satisfy the privacy of each of the analysis requester and the analyst 120 and the request of the knowledge property security grade by controlling the number of composites for protecting the target nucleic acid sequence, the number of target elements included in the plurality of composites, or the number of disguising elements included in each composite. That is, the present invention can satisfy the security of the nucleic acid sequence of the analysis requester and the request of knowledge property security of the analyst 120 simultaneously by controlling the number of target elements, the number of disguising elements, and the number of composites.

For example, FIG. 3 illustrates the creation of six composites by the composite creator 212, and here, composites C1 to C5 each include one target element and about four disguising elements, and composite C6 includes only four disguising elements. Here, the information protection grade of the target nucleic acid sequence of six composites including composite C6 not containing a target element is 4^6=2^12=1/4096, and corresponds to the 12-bit security level. If the target security level is set to a very strong 32-bit level, 2^32=4^16=16^8=256^4=65546^2, thereby creating 32 composites each including 2 elements, 16 composites each including 4 elements, 8 composites each including 16 elements, 4 composites each including 256 elements, or 2 composites each including 65546 elements, thus satisfying a 32-bit security level.

Therefore, according to the present invention, after the information protection grade is first set, the number of composites and the number of elements included in the composite may be determined in consideration of the calculation load of the analyst 120.

Figure 4:
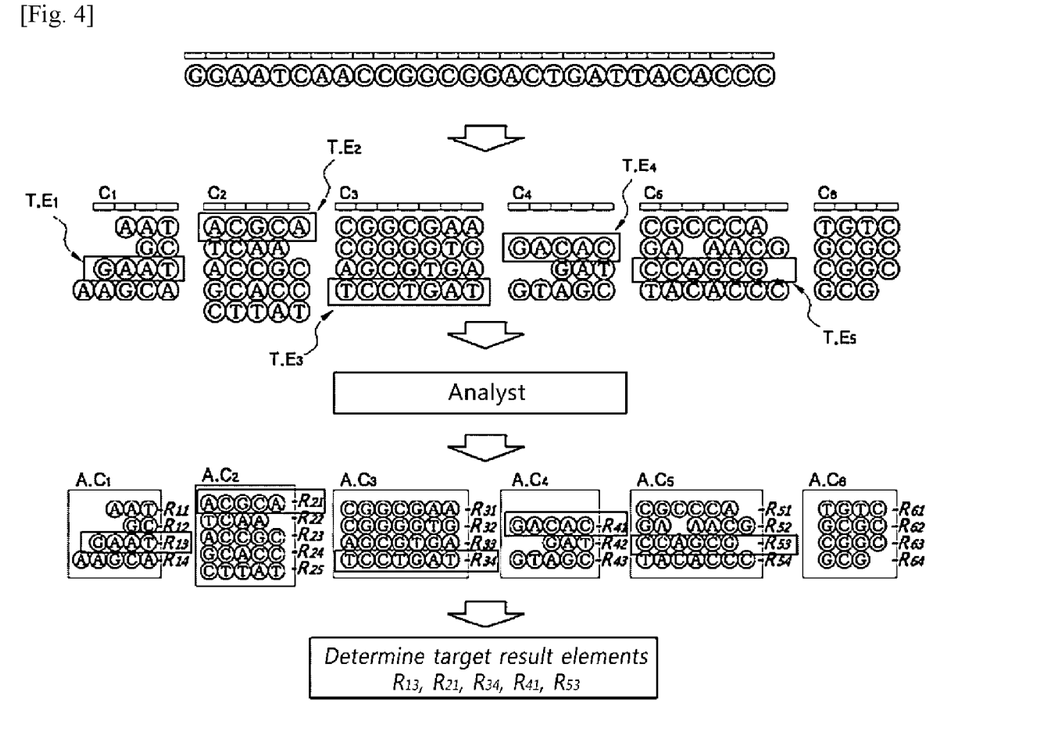
FIG. 4 is a diagram illustrating the creation of a plurality of composites and an interpretation procedure of a plurality of analysis composites according to another embodiment of the present invention.

FIG. 4 is a diagram illustrating the creation of a plurality of composites and an interpretation procedure of a plurality of analysis composites according to another embodiment of the present invention.

In FIG. 4, the composite creator 212 creates the target elements by segmenting the nucleic acid sequence of the analysis requester into partial nucleotides. The composite creator 212, in order to create a plurality of composites, may create target element T.E1 having a nucleic acid sequence of GGAA, target element T.E2 having a nucleic acid sequence of TCAAC, target element T.E3 having a nucleic acid sequence of CGGCGGA, target element T.E4 having a nucleic acid sequence of CTGAT, and target element T.E5 having a nucleic acid sequence of TACACCC, in a manner of segmenting the nucleic acid sequence of the analysis requester into partial nucleotides. Hereinafter, the procedure carried out by the nucleic acid sequence security apparatus 110 is shown in FIG. 3.

Figure 5A:
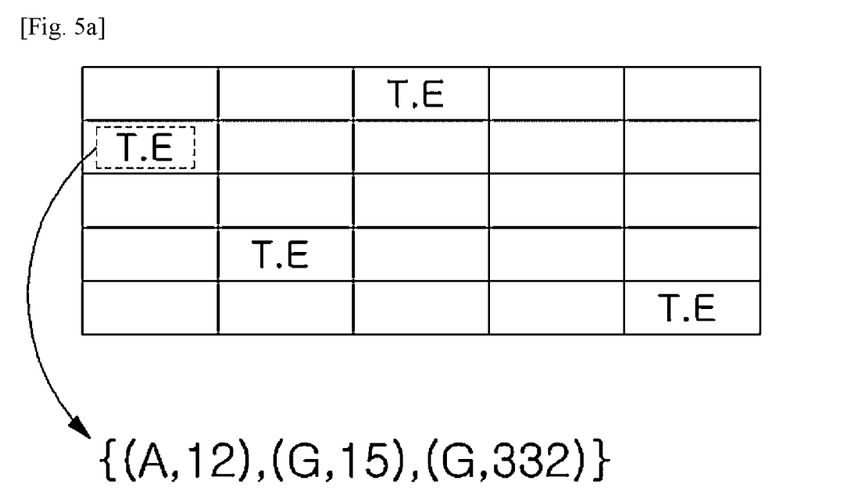
FIG. 5a is a diagram visualizing a sparse matrix with respect to target elements according to an embodiment of the present invention.
Figure 5B:
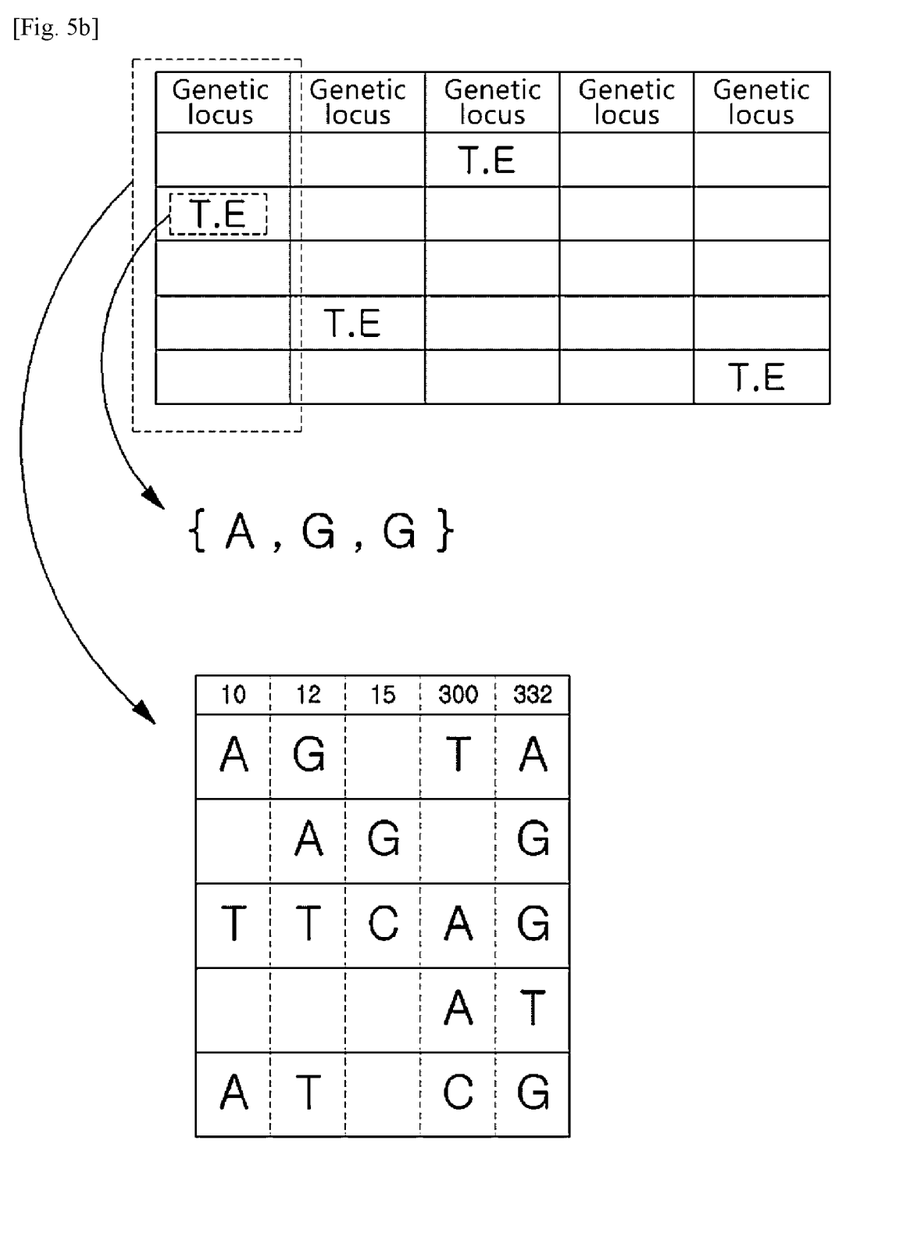
FIG. 5b is a diagram visualizing a sparse matrix with respect to target elements according to another embodiment of the present invention.

FIG. 5a is a diagram visualizing a sparse matrix with respect to target elements according to an embodiment of the present invention, and FIG. 5b is a diagram visualizing a sparse matrix with respect to target elements according to another embodiment of the present invention.

In FIG. 5a, the composite creator 212 may define a target element cell on the sparse matrix as a nucleotide-locus set including at least one nucleotide and genetic locus of a target element. For example, with respect to a target element cell on the sparse matrix, if a corresponding target element corresponds to a nucleic acid sequence composed of nucleotide A with a genetic locus of 12, nucleotide G with a genetic locus of 15, and nucleotide G with a genetic locus of 332, the corresponding target element may be defined as a set of {(A,12), (G,15), (G,332)}.

In FIG. 5b, the composite creator 212 may define a target element cell on the sparse matrix as at least one nucleotide set associated with a genetic locus. For example, with respect to a target element cell on the sparse matrix, if a corresponding target element corresponds to a nucleic acid sequence composed of nucleotide A with a genetic locus of 12, nucleotide G with a genetic locus of 15, and nucleotide G with a genetic locus of 332, the corresponding target element may be defined as a set of {A, G, G}. Here, the genetic loci 12, 15, and 332 of the corresponding nucleotides may be commonly expressed on the matrix.

Figure 6:
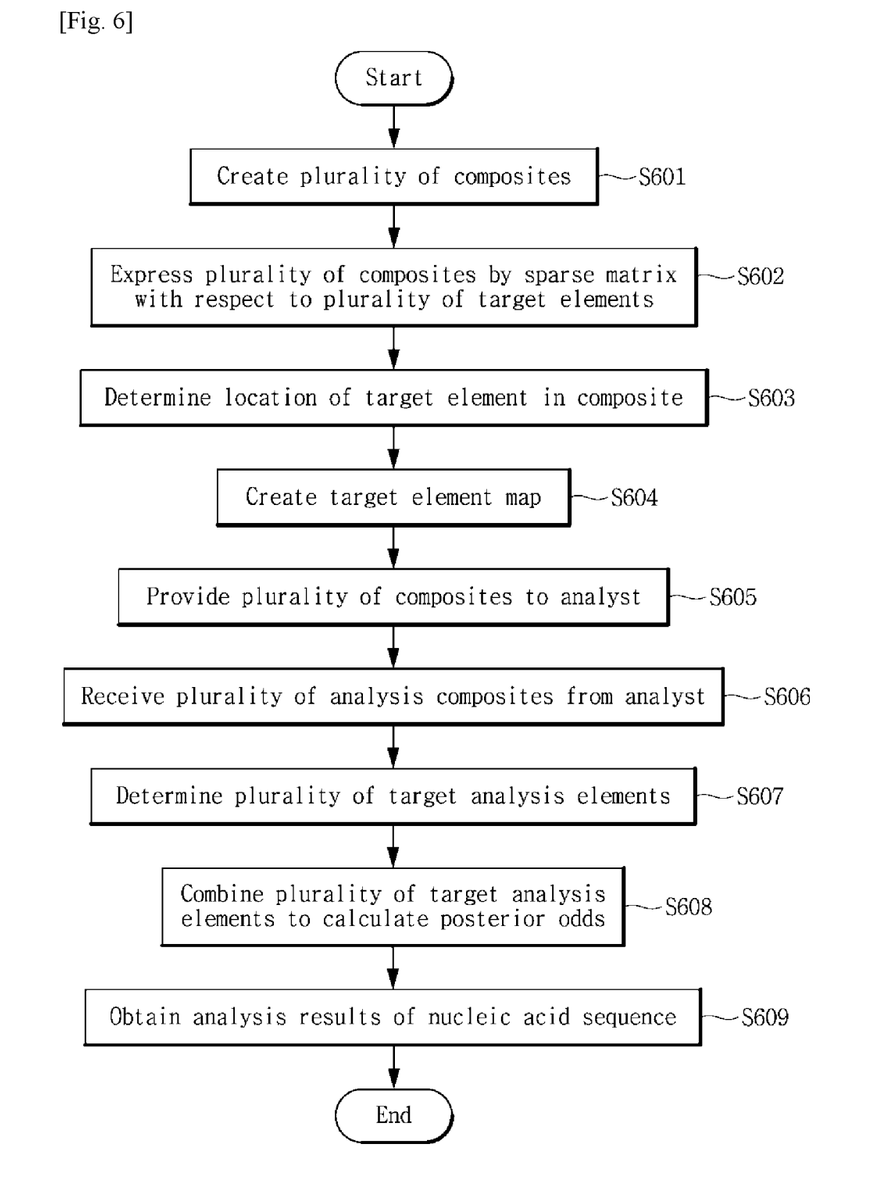
FIG. 6 is a flowchart illustrating a nucleic acid sequence security method carried out by the nucleic acid sequence security apparatus in FIG. 2.

FIG. 6 is a flowchart illustrating a nucleic acid sequence security method carried out by the nucleotide sequence security apparatus in FIG. 2.

The composite creator 212 creates a plurality of composites each including at least one of target elements derived from the nucleic acid sequence of the analysis requester or disguising elements identical to or different from the target elements (S601). Here, the composite creator 212 may express the plurality of composites by a sparse matrix with respect to a plurality of target elements (S602).

The composite creator 212 may determine the location of a corresponding target element in the corresponding composite if the target element is included in the created composite (S603). The composite creator 212, while expressing the plurality of composites by a sparse matrix with respect to the plurality of target elements, may dynamically determine the location of a target element cell on the sparse matrix, thereby creating a target element map necessary for a decoding procedure (S604).

The composite provider 214 may provide the created plurality of composites to the analyst, and the interpretation receiver 216 may receive the plurality of analysis composites showing the interpretation results of the plurality of composites from the analyst (S605 and S606).

The interpretation composite interpreter 218 may determine a plurality of target analysis elements showing the interpretation results of the plurality of target elements on the basis of location information of the target elements stored in the target element map (S607). The interpretation composite interpreter 218 may calculate the posterior odds of the analyst requester by combining the determined plurality of target analysis elements, and may obtain the final analysis results of the nucleic acid sequence of the analysis requester through the calculated posterior odds (S608 and S609).

Although the embodiments of the present invention have been described with reference to the accompanying drawings, it should be understood that various changes and modifications by those skilled in the art could be made without departing from the spirit and scope of the present invention as defined by the following claims.

INDUSTRIAL APPLICABILITY

The present invention relates to nucleic acid sequence security technology and, more specifically, to a nucleic acid sequence security method capable of analyzing a nucleic acid sequence of an analysis requester without exposing the nucleic acid sequence of the analysis requester to an analyst, to a nucleic acid sequence security apparatus, and to a recording medium storing the same.

The invention claimed is:

1. A method for secure communication of nucleic acid sequence information of an analysis requester to an analyst, the method comprising steps of:
   (a) obtaining a nucleic acid sequence of the analysis requester;
   (b) identifying one or more target elements in the nucleic acid sequence, wherein each of the target elements comprises sequence data derived from the nucleic acid sequence;
   (c) obtaining one or more disguising elements, wherein each of the disguising elements comprises sequence data, the sequence data of the disguising elements being different from the sequence data of the target elements identified;
   (d) creating a plurality of original composites of sequence data, at least one of the plurality of original composites comprising at least one of the target elements and at least one of the disguising elements arranged to disguise the target elements within the original composites;
(e) creating a matrix with data related to the target elements in the original composites, wherein data stored in the matrix comprise an entire or a partial nucleotide sequence of a target element or a genetic locus of a target element;
(f) creating a target element map indicating a location within the matrix, where data related to a target element is stored; and
(g) transmitting the plurality of original composites to the analyst through a network.

2. The method of claim 1, wherein the data stored in the matrix comprise an entire or a partial nucleotide sequence of a target element and a genetic locus of the target element.

3. The method of claim 1, wherein step (b) further comprises extracting an entire or a partial nucleotide sequence of a target element or a genetic locus of a target element.

4. The method of claim 1, wherein step (b) further comprises identifying a segment of the nucleic acid sequence, thereby creating a target element.

5. The method of claim 1, wherein in step (c), the one or more disguising elements are selectively obtained based on a genetic distance or evolutionary distance from the target elements.

6. The method of claim 1, wherein in step (d), a total number of the original composites or a size of each of the original composites is determined according to a security strength set by the analysis requester.

7. The method of claim 1, further comprising following transmitting of the plurality of original composites to the analyst, receiving back from the analyst a plurality of analysis composites.

8. The method of claim 7, further comprising interpreting the analysis composites from the analyst by identifying one or more target analysis elements related to each of the one or more target elements using the target element map, wherein each target analysis element is data obtained by analysis of a target element.

9. An apparatus for secure communication of nucleic acid sequence information of an analysis requester to an analyst, the apparatus comprising:
a processor; and
a computer-readable recording medium storing code that, when executed by the processor, causes the processor to perform the steps of:
(a) obtaining a nucleic acid sequence of the analysis requester;
(b) identifying one or more target elements in the nucleic acid sequence, wherein each of the target elements comprises sequence data derived from the nucleic acid sequence;
(c) obtaining one or more disguising elements, wherein each of the disguising elements comprises sequence data, the sequence data of the disguising elements being different from the sequence data of the target elements identified;
(d) creating a plurality of original composites of sequence data, at least one of the plurality of original composites comprising at least one of the target elements and at least one of the disguising elements arranged to disguise the target elements within the original composites;
(e) creating a matrix with data related to the target elements in the original composites, wherein data stored in the matrix comprise an entire or a partial nucleotide sequence of a target element or a genetic locus of a target element;
(f) creating a target element map indicating a location within the matrix, where data related to a target element is stored; and
(g) transmitting the plurality of original composites to the analyst through a network.

10. The apparatus of claim 9, wherein the code, when executed by the processor, causes the processor to further perform following transmitting of the plurality of original composites to the analyst, receiving back from the analyst a plurality of analysis composites.

11. The apparatus of claim 10, wherein the code, when executed by the processor, causes the processor to further perform interpreting the analysis composites from the analyst by identifying target analysis elements related to a target element composites using the target element map, wherein each target analysis element is data obtained by analysis of a target element.

12. A non-transitory computer-readable recording medium storing a computer program for secure communication of nucleic acid sequence information of an analysis requester to an analyst, the stored program configured so that, when the program is executed by a processor, the processor performs the steps of:
(a) obtaining a nucleic acid sequence of the analysis requester;
(b) identifying one or more target elements in the nucleic acid sequence, wherein each of the target elements comprises sequence data derived from the nucleic acid sequence;
(c) obtaining one or more disguising elements, wherein each of the disguising elements comprises sequence data, the sequence data of the disguising elements being different from the sequence data of the target elements identified;
(d) creating a plurality of original composites of sequence data, at least one of the plurality of original composites comprising at least one of the target elements and at least one of the disguising elements arranged to disguise the target elements within the original composites;
(e) creating a matrix with data related to the target elements in the original composites, wherein data stored in the matrix comprise an entire or a partial nucleotide sequence of a target element or a genetic locus of a target element;
(f) creating a target element map indicating a location within the matrix, where data related to a target element is stored; and
(d) transmitting the plurality of original composites to the analyst through a network.

13. The non-transitory computer-readable recording medium of claim 12, when the program is executed by the processor, the processor further receives back from the analysis a plurality of analysis composites following transmitting of the plurality of original composites to the analyst for analysis.

* * * * *